(12) United States Patent
Zhou et al.

(10) Patent No.: US 11,142,542 B2
(45) Date of Patent: Oct. 12, 2021

(54) METHOD FOR SYNTHESIZING SUCROSE-6-ESTER

(71) Applicants: Zhejiang Nhu Company Ltd., Zhejiang (CN); Shandong Nhu Fine Chemical Science and Technology Company Ltd., Shandong (CN)

(72) Inventors: Yougui Zhou, Shandong (CN); Jiang Cai, Zhejiang (CN); Kaifeng Ma, Zhejiang (CN); Yugang Wang, Shandong (CN); Xiaoqiao Wei, Zhejiang (CN); Yunhan Yang, Zhejiang (CN)

(73) Assignees: Zhejiang Nhu Company Ltd., Zhejiang (CN); Shandong Nhu Fine Chemical Science and Technology Company Ltd., Shandong (CN)

( * ) Notice: Subject to any disclaimer, the term of this patent is extended or adjusted under 35 U.S.C. 154(b) by 0 days.

(21) Appl. No.: 16/981,986

(22) PCT Filed: Apr. 24, 2019

(86) PCT No.: PCT/CN2019/084014
§ 371 (c)(1),
(2) Date: Sep. 17, 2020

(87) PCT Pub. No.: WO2019/223485
PCT Pub. Date: Nov. 28, 2019

(65) Prior Publication Data
US 2021/0002317 A1 Jan. 7, 2021

(30) Foreign Application Priority Data
May 22, 2018 (CN) .......................... 201810494829.X

(51) Int. Cl.
*C07H 1/06* (2006.01)
*C07H 5/02* (2006.01)
(52) U.S. Cl.
CPC ........ *C07H 1/06* (2013.01); *C07H 5/02* (2013.01)
(58) Field of Classification Search
CPC ................................... C07H 1/06; C07H 5/02
See application file for complete search history.

(56) References Cited

U.S. PATENT DOCUMENTS

| 5,023,329 | A | 6/1991 | Neiditch et al. |
| 5,034,551 | A | 7/1991 | Vernon et al. |
| 2011/0087018 | A1 | 4/2011 | Micinski et al. |
| 2012/0095199 | A1 | 4/2012 | Hutton et al. |

FOREIGN PATENT DOCUMENTS

| CN | 101979396 A | 2/2011 |
| CN | 102365292 A | 2/2012 |
| CN | 102584910 A | 7/2012 |
| CN | 102639550 A | 8/2012 |
| CN | 104098617 A | 10/2014 |
| CN | 108558962 A | 9/2018 |
| WO | 2009035503 A1 | 3/2009 |

OTHER PUBLICATIONS

Streuli, C.A., Analytical Chemistry, 1960, 32(8), p. 985-987. (Year: 1960).*
International Search Report and Written Opinion of the International Searching Authority issued in International App. No. PCT/CN2019/084014; dated Aug. 5, 2019; 16 pages, including English translation of International Search Report.
Office Action issued in Chinese Patent Application No. 201810494829. X; dated Nov. 28, 2019; 16 pages including English translation.
Lu Guoyuan; editor; "Phosporus-Containing Compounds"; Organic Chemistry, Nanjing University Press; Dec. 1999; 4 pages.

* cited by examiner

*Primary Examiner* — Jonathan S Lau
(74) *Attorney, Agent, or Firm* — Ulmer & Berne LLP

(57) ABSTRACT

A method for synthesizing sucrose-6-ester includes: (a) in the presence of a polar aprotic solvent, contacting an organic phosphine compound represented by formula I with sucrose and an organic tin compound; (b) removing water to obtain a reaction liquid containing a tin-sucrose adduct; and (c) contacting the reaction liquid containing the tin-sucrose adduct with an acid anhydride compound to prepare a sucrose-6-ester. In formula I, $R^1$, $R^2$, and $R^3$ each are a linear or branched alkyl having 1 to 20 carbon atoms, a cycloalkyl having 3 to 10 carbon atoms, or an aryl having 6 to 10 carbon atoms; moreover, the $R^1$, $R^2$, and $R^3$ are identical groups, partially identical groups, or different groups from each other. According to the method, the reaction conversion rate and selectivity are greatly improved; moreover, it is easy to realize industrial application.

20 Claims, 1 Drawing Sheet

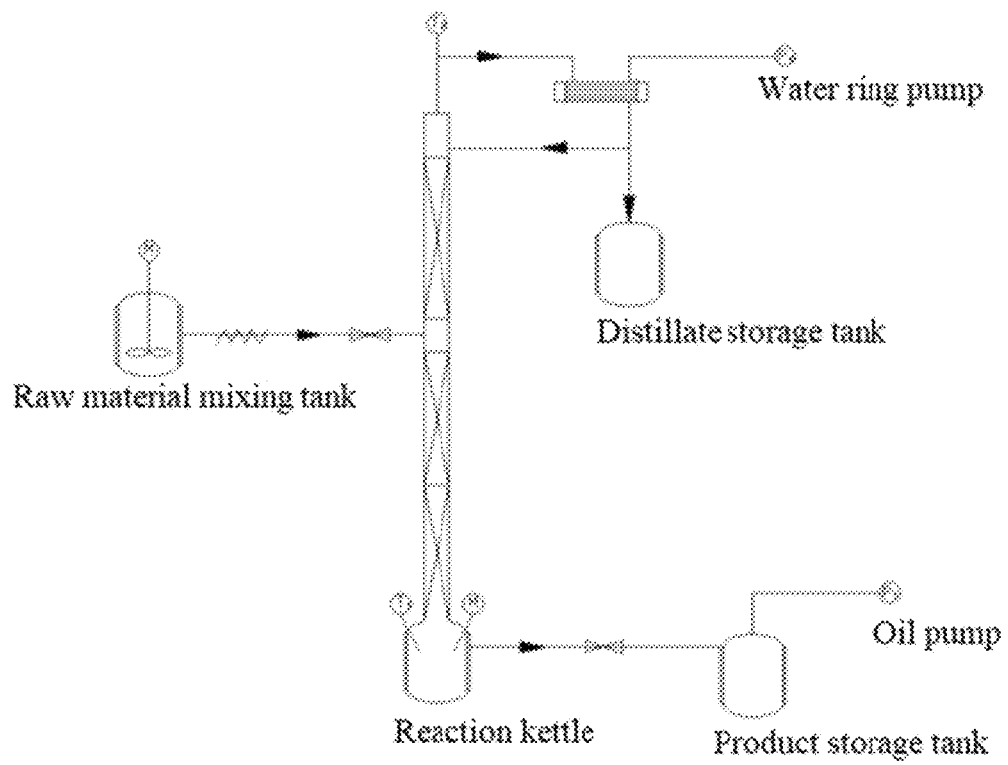

METHOD FOR SYNTHESIZING SUCROSE-6-ESTER

TECHNICAL FIELD

The present disclosure relates to a method for selectively synthesizing sucrose-6-ester, and specifically to sucrose-6-ester used in the preparation of an advanced sweetener trichlorogalactosucrose.

BACKGROUND

Trichlorogalactosucrose (4,1',6'-trichloro-4,1',6'-trideoxy-galactose, abbreviated as a sucralose) is a high-intensity food sweetener, the sweetness of the sweetener is 600 times that of sucrose, and the sweetener has the characteristics of no energy, safety, good stability, pure sweet taste, extremely low probability of being absorbed by human bodies and the like, and is one of the most excellent functional sweeteners currently. Trichlorogalactosucrose is successfully developed by Tate & Lyle in 1976, successfully put into the market in 1988, and is currently approved to be produced and used in a plurality of countries and regions all over the world.

The main production methods of trichlorogalactosucrose include a hologroup protected synthesis method and a monogroup protected synthesis method. Although the hologroup protected synthesis method has mild reaction conditions, the reaction steps are complicated, the reaction yield is low, and the reaction selectivity is poor. The monogroup protected synthesis method is used for synthesizing the sucralose, has the characteristics of few reaction steps, simple operation process, high reaction selectivity and high yield, and is suitable for industrial production. The sucrose-6 ester is the most important intermediate for synthesizing the sucralose by the monogroup protected synthesis method.

A method for synthesizing sucrose-6-ester using an organic tin compound as a catalyst has been disclosed in Patent US 20110087018 and Patent US 20120095199, respectively.

The method disclosed in US 20110087018 comprises the following steps in sequence: (a) providing a first reaction mixture comprising sucrose, a polar aprotic solvent, and an organic tin compound; (b) removing water from the first reaction mixture to provide a second reaction mixture that is substantially free of water; and (c) adding a carboxylic acid anhydride to the second reaction mixture to provide a third reaction mixture, thereby producing a sucrose-6-ester; wherein a non-polar co-solvent is not added during step (b); and in step (b), the temperature does not exceed about 80° C.

The method disclosed in US 20120095199 comprises the following steps in sequence: (a) contacting sucrose with an organotin-based acylation promoter in a solvent comprising a tertiary amide and comprising a hydrocarbon solvent in the presence of a compound selected from amines and basic alkali metal salts; (b) removing water to form a tin-sucrose adduct; and (c) contacting the tin-sucrose adduct with an acylating agent to form a sucrose-6-ester. The amines and the basic alkali metal salts may be alkali metal carbonates, alkali metal hydroxides, alkali metal carboxylates, amines (meeting the boiling point requirement) and the like. However, the alkali metal salt or alkali meal hydroxide used in said method is insoluble in the reaction system, and it is difficult to continue the reaction using equipment because it is a heterogeneous system.

SUMMARY

The object of the present disclosure is to provide a method for preparing sucrose-6-ester, which is simpler and more economical and has high reaction yield aiming at the defects of the prior art.

The present disclosure provides a method for synthesizing sucrose-6-ester, and the method comprises:

(a) in the presence of a polar aprotic solvent, contacting an organic phosphine compound represented by formula I with sucrose and an organic tin compound;

(b) removing water to obtain a reaction liquid containing a tin-sucrose adduct; and (c) contacting the reaction liquid containing the tin-sucrose adduct with an acid anhydride compound to prepare a sucrose-6-ester;

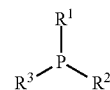

In formula I, $R^1$, $R^2$, and $R^3$ are each a linear or branched alkyl having 1 to 20 carbon atoms, a cycloalkyl having 3 to 10 carbon atoms or an aryl having 6 to 10 carbon atoms, preferably a linear or branched alkyl having 1 to 12 carbon atoms, a cycloalkyl having 3 to 6 carbon atoms or an aryl having 6 to 7 carbon atoms, more preferably methyl, ethyl, propyl, n-butyl, isobutyl, tert-butyl, hexyl, cyclohexyl, octyl, n-undecyl, phenyl, p-methylphenyl, or p-methoxyphenyl, and most preferably phenyl, p-methylphenyl, n-butyl, or cyclohexyl; and the $R^1$, $R^2$, and $R^3$ are identical groups, partially identical groups, or different groups from each other.

According to the method for synthesizing sucrose-6-ester provided by the present disclosure, the organic phosphine compound is triphenylphosphine, tricyclohexylphosphine, or tributylphosphine.

According to the method for synthesizing sucrose-6-ester provided by the present disclosure, a molar ratio of an amount of the organic phosphine compound I to an amount of the sucrose is 0.02 to 0.15:1; preferably 0.03 to 0.07:1.

According to the method for synthesizing sucrose-6-ester provided by the present disclosure, the polar aprotic solvent is N,N-dimethylformamide, N,N-dimethylacetamide, or dimethyl sulfoxide; preferably N,N-dimethylformamide; and the molar ratio of an amount of the polar aprotic solvent to an amount of the sucrose is 2 to 100:1, preferably 30 to 65:1, and more preferably 40 to 50:1.

According to the method for synthesizing sucrose-6-ester provided by the present disclosure, the organic tin compound is 1,3-diacetoxy-1,1,3,3-tetrakis(C1-C8)alkyldistannoxane; preferably 1,3-diacetoxy-1,1,3,3-tetrabutyldistannoxane or 1,3-diacetoxy-1,1,3,3-tetraoctyldistannoxane; and a molar ratio of an amount of the organic tin compound to an amount of the sucrose is 0.5 to 3.0:1; preferably 0.7 to 1.1:1.

According to the method for synthesizing sucrose-6-ester provided by the present disclosure, the removing of water in the step (b) is carried out intermittently, or continuously; preferably the removing of water is carried out continuously; and more preferably the removing of water is carried out by continuous distillation.

According to the method for synthesizing sucrose-6-ester provided by the present disclosure, the removing of water in the step (b) is carried out under conditions of a temperature of 45 to 90° C. and a pressure of 1 to 300 KPa; preferably, the removing of water is carried out under conditions of a temperature of 50 to 80° C. and a pressure of 5 to 50 KPa.

According to the method for synthesizing sucrose-6-ester provided by the present disclosure, in the step (b), the removing of water is carried out so that the water content in the reaction liquid containing the tin-sucrose adduct is ≤0.3 wt %.

According to the method for synthesizing sucrose-6-ester provided by the present disclosure, in the step (c), the acid anhydride compound is acetic anhydride or benzoic anhydride; and a molar ratio of an amount of the acid anhydride compound to an amount of the sucrose is 0.80~1.50:1; preferably 1.08~1.17:1.

According to the method for synthesizing sucrose-6-ester provided by the present disclosure, in the step (c), a reaction temperature is −10 to 20° C., and a reaction time is 1 to 10 h; preferably, the reaction temperature is −5 to 10° C., and the reaction time is 2 to 6 h.

Compared with the prior art, the present disclosure has excellent technical effects that:

(1) in the process of preparing the sucrose-6-ester, a reaction promoter organic phosphine compound is adopted, the conversion rate and selectivity of the reaction are greatly improved, and the molar yield of the sucrose-6-ester may reach 92% or more and even as high as 95.3%;

(2) the organic phosphine compound used as the reaction promoter may be dissolved in a polar aprotic solvent, and the reaction for preparing the sucrose-6-ester is a homogeneous reaction, so that the problem of possible blockage of the traditional solid alkaline cocatalyst used in a reaction system is avoided, the method for preparing the sucrose-6-ester with higher selectivity is realized, and the method is easy to realize industrial application.

BRIEF DESCRIPTION OF THE DRAWINGS

FIG. 1 shows a partial flow diagram of an embodiment of the present disclosure.

DETAILED DESCRIPTION

The method for synthesizing sucrose-6-ester provided by the present disclosure comprises:

(a) in the presence of a polar aprotic solvent, contacting an organic phosphine compound represented by formula I with sucrose and an organic tin compound;

(b) removing water to obtain a reaction liquid containing a tin-sucrose adduct; and (c) contacting the reaction liquid containing the tin-sucrose adduct with an acid anhydride compound to prepare a sucrose-6-ester;

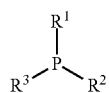

I

In formula I, $R^1$, $R^2$, and $R^3$ are each an alkyl or an aryl having 1 to 20 carbon atoms. Examples of alkyls include methyl, ethyl, propyl, n-butyl, isobutyl, tert-butyl, hexyl, cyclohexyl, octyl, or n-undecyl; examples of aryls include phenyl, p-methylphenyl, or p-methoxyphenyl and the like; among the above alkyls and aryls, phenyl, p-methylphenyl, n-butyl, or cyclohexyl are preferable; and the $R^1$, $R^2$, and $R^3$ are identical groups, partially identical groups, or different groups from each other.

According to the method for synthesizing sucrose-6-ester provided by the present disclosure, in step (a), the organic phosphine compound is adopted as a reaction promoter, therefore, the reaction between the sucrose and the organic tin compound can be promoted, a tin-sucrose adduct is formed and the conversion of the sucrose is promoted, so that the yield of the final product sucrose-6-ester is improved. In addition, said organic phosphine compound can be dissolved in the polar aprotic solvent, therefore, the homogeneous reaction can be performed to prepare a sucrose-6-ester, so that the reaction efficiency is high, and the reaction is easy to realize continuity.

Thereinto, the organic phosphine compound is preferably triphenylphosphine, tricyclohexylphosphine, or tributylphosphine, which is relatively low cost and easily available.

The molar ratio of the amount of the organic phosphine compound I to the amount of the sucrose is preferably 0.02 to 0.15:1. Since the molar ratio of the two amounts within said range, the conversion rate of the sucrose can be sufficiently improved to improve the yield of the sucrose-6-ester, and the effect of promoting the conversion of the sucrose is poor when the molar ratio is lower than the lower limit or higher than the upper limit. The molar ratio of the two amounts is further preferably 0.03 to 0.07:1.

In step (a), the polar aprotic solvent is selected as a solvent of the reaction system, which may dissolve sucrose, an organic tin compound, an organic phosphine compound, and a tin-sucrose adduct. The molar ratio of the amount of the polar aprotic solvent to the amount of the sucrose is preferably 2 to 100:1. Since the molar ratio of the two amounts within said range, each reactant and reaction promoters, such as sucrose, organic tin compounds and organic phosphine compounds, and acid anhydride compounds, can be fully dissolved in the polar aprotic solvent, thereby realizing a homogeneous reaction and being beneficial to perform the reaction. If the molar ratio is lower than the lower limit, there is a possibility that each reactant and reaction promoter may not be completely dissolved, thereby affecting the reaction efficiency; if the molar ratio is higher than the upper limit, too much polar aprotic solvent is present in the reaction system, thereby increasing the burden of separating the product sucrose-6-ester. The molar ratio of the two amounts is further more preferably 30 to 65:1, and most preferably 40 to 50:1.

The polar aprotic solvent may be selected from those known to persons skilled in the art. Suitable polar aprotic solvents may include, for example, N,N-dimethylformamide, N,N-dimethylacetamide, or dimethyl sulfoxide; preferably N,N-dimethylformamide.

The organic tin compound and the sucrose can form a tin-sucrose adduct. The molar ratio of the amount of the organic tin compound to the amount of the sucrose is preferably 0.5 to 3.0:1. Since the molar ratio of the two amounts within said range, the sucrose can be fully reacted, thereby promoting the conversion of the sucrose and reducing the amount of the unreacted sucrose. If the molar ratio is lower than the lower limit, there is a possibility that the amount of the unreacted sucrose increases; if the molar ratio is higher than the upper limit, the waste of raw materials is generated, and the burden of separating the product sucrose- 6-ester is increased. The molar ratio of the two amounts is further more preferably 0.7 to 1.1:1.

The organic tin compound may be selected from those known to persons skilled in the art. Suitable organic tin compounds include, for example, 1,3-diacetoxy-1,1,3,3-tetrakis(C1-C8)alkyldistannoxane, preferably 1,3-diacetoxy-1,1,3,3-tetrabutyldistannoxane or 1,3-diacetoxy-1,1,3,3-tetraoctyldistannoxane.

According to the method for synthesizing sucrose-6-ester provided by the present disclosure, in step (b), removing of water can allow the reaction to proceed rapidly in the direction of obtaining a tin-sucrose adduct and can prevent the acid anhydride compound added in the subsequent step (c) from hydrolyzing into the corresponding carboxylic acid, so that a sufficient amount of sucrose-6-ester can be obtained as a product. When the water is removed so that the water content in the reaction liquid containing the tin-sucrose adduct is ≤0.3 wt %, the reaction step (b) is stopped and the resulting reaction liquid is subjected to step (c).

As regards the method of removing water, various methods known to those skilled in the art can be employed, and the removing of water can be carried out intermittently, or can be carried out continuously. Preferably, the removing of water is carried out continuously; more preferably, the removing of water is carried out by a continuous distillation method. The water removal method of said continuous distillation of has a distillate extraction rate of between 10% and 40%, and preferably between 20% and 30%. The water removal method of continuous distillation is carried out in a distillation column, and the packing in the distillation column may be random packing, such as Raschig rings, Pall rings, cascade rings, rectangular saddle rings, arc saddle rings and the like; regular packings, such as CY, BX, AY, plate corrugations, Mellapak packings, etc., are also possible.

As regards the operation conditions of removing water, the operation for removing water is preferably performed at a lower temperature in order to reduce thermal decomposition of carbohydrates. For example, the operation conditions are preferably that the temperature is 45 to 90° C. and the pressure is 1 to 300 KPa; more preferably, the operation of removing water is carried out under reduced pressure and at a lower temperature, wherein the operation conditions are that the temperature is 50 to 80° C. and the pressure is 5 to 50 KPa.

In step (b), an embodiment is more preferably that removing of water is carried out in a distillation column, a extracted material rich in tin-sucrose adduct is extracted from the bottom of the distillation column, said extracted material is mixed with the residual material in the bottom of the distillation column to obtain a reaction liquid containing a tin-sucrose adduct, and then the reaction liquid containing the tin-sucrose adduct is subjected to step (c). By this preferred embodiment, the addition reaction can be promoted to proceed in the direction of the reaction product, and at the same time, by mixing the extracted material with the residual material of the column bottom, the conversion rate of the reactant and the yield of the reaction product can be improved.

According to the method for synthesizing sucrose-6-ester of the present disclosure, in step (c), the molar ratio of the amount of the acid anhydride compound to the amount of the sucrose is preferably 0.80 to 1.50:1. Since the molar ratio of the two amounts within said range, the reaction for producing sucrose-6-ester can be proceeds sufficiently to yield a sufficient amount of the product of sucrose-6-ester. If the molar ratio is lower than the lower limit, the residual sucrose is increased, and the conversion rate of non-target product monoester is increased; if the molar ratio is higher than the upper limit, the conversion rate of sucrose generated by excessive carboxylation is increased. The molar ratio of the two amounts is further more preferably 1.08 to 1.17:1.

The acid anhydride compound known to those skilled in the art may be adopted. Suitable acid anhydride compounds include, for example, acetic anhydride or benzoic anhydride; more preferably acetic anhydride.

As regards the operation conditions in step (c), in a preferred case, in order to prevent the deterioration of selectivity caused by excessively fast reaction rate, in step (c), a reaction temperature is −10 to 20° C., and a reaction time is 1 to 10 h; more preferably, the reaction temperature is −5 to 10° C., and the reaction time is 2 to 6 h.

According to the method for synthesizing sucrose-6-ester of the present disclosure, in a preferred case, in step (a), the organic phosphine compound represented by formula I is contacted with sucrose and an organic tin compound in the presence of a polar aprotic solvent to carry out a reaction, and the step (b) is carried out while the reaction is carried out in the step (a), and water obtained in the reaction is removed to promote the reaction in the direction of obtaining a reaction product, thereby obtaining the reaction liquid containing the tin-sucrose adduct.

A preferred embodiment of the present disclosure will be described below with reference to FIG. 1 as follows:

step (a), sucrose is dissolved in N,N-dimethylformamide (DMF) with the amount of 80 to 85 mol % of the total amount at the temperature of 60 to 80° C., and an organic tin compound is dissolved in DMF with the amount of 15 to 20 mol % of the total amount at the temperature of 30 to 50° C. The above two solutions are uniformly mixed in a raw material mixing tank under the condition where the temperature is kept at 40 to 60° C., then an organic phosphine compound is added into the mixture, stirred and dissolved;

step (b), the mixed solution obtained in the step (a) is allowed to enter a vacuum distillation column with a reaction kettle at the bottom for reaction, and the vacuum distillation is performed continuously to remove water obtained in the reaction, wherein a water ring pump provides the system a negative pressure. The operation conditions for the distillation column are that the temperature of the bottom of the column is 60 to 70° C., and the pressure in the column is 5 to 50 KPa. Water and part of DMF solvent are extracted from the top of the column and are fed into a distillate storage tank, and heating is stopped when the water content of the reaction liquid containing the tin-sucrose adduct obtained from the bottom of the column is 0.3 wt % or less. The residual material at the bottom of the reaction kettle is uniformly mixed with the extracted material to obtain the reaction liquid containing the tin-sucrose adduct, the reaction liquid is fed into a product storage tank, and the reaction liquid is pumped out through an oil pump.

step (c), the reaction liquid containing the tin-sucrose adduct is cooled to −5 to 10° C., at this time, an acid anhydride compound is dropwise added thereto, and the reaction is carried out for 2 to 6 hours while keeping the temperature, and then the reaction is stopped by adding water.

The present disclosure is further described below by way of example, but the present disclosure is not limited to the embodiments described below.

Sucrose and esterification products of sucrose in the following examples and comparative examples were analyzed using high performance liquid chromatography.

Example 1 (Adopting Triphenylphosphine as an Organic Phosphine Compound)

407.4 g (1.19 mol) of sucrose was taken and dissolved in 3542.0 g (48.46 mol) of DMF at 70° C., and 585.9 g (0.98 mol) of 1,3-diacetoxy-1,1,3,3-tetrabutyldistannoxane was taken and dissolved in 713.0 g (9.76 mol) of DMF at 40° C. The above two solutions were uniformly mixed under the condition where the temperature was kept at 50° C., then 15.6 g (0.059 mol) of triphenylphosphine was added thereto, stirred and dissolved to obtain a DMF mixed solution containing sucrose, an organic tin compound, and triphenylphosphine.

150.0 g of DMF was taken to feed into bottom of a vacuum distillation column (the diameter of the column is 25 mm, the distillation section is 30 cm, the stripping section is 50 cm, and a glass spring filler), a water ring pump was used to vacuumize to ensure that the pressure in the column is 5 to 50 KPa, and DMF was heated in an oil bath at the temperature of 95° C., the bottom of the column was regulated for total reflux for 15 to 30 min, and the temperature in the bottom of the column was controlled to be 60 to 70° C. The above mixed solution of which the temperature was kept still was preheated by a water bath coil pipe at 85° C., and the mixed solution was fed at the speed of 9 g/min to enable the mixed solution to react in a reaction kettle, extracting from the top of the column started while feeding, and the extraction rate of distillates was regulated to 27%. After 150 g of the raw materials were fed, the reaction mixed solution was started to be extracted from the bottom of the kettle, and an automatic control system was adopted for controlling to keep the feeding and discharging materials constant. After the raw materials were fed in, 50 g of DMF was taken to flush the pipeline, fully extracting from the top of the column was conducted for 10 min, the heating was stopped, and the temperature of the bottom of the column was reduced to the room temperature, then the residual materials at the bottom of the kettle was uniformly mixed with the extracted materials to obtain the reaction liquid containing the tin-sucrose adduct.

The reaction liquid containing the tin-sucrose adduct was cooled to 0° C., and 138.5 g (1.36 mol) of acetic anhydride was slowly added dropwise thereto, and the temperature was kept for 4 h after completion of the addition, and 321.4 g of water was added to terminate the acylation reaction. Then, cyclohexane (2000 mL×3) was added to extract and recover the organic tin compound 1,3-diacetoxy-1,1,3,3-tetrabutyl di stannoxane, the molar yield of the sucrose-6-acetate detected by HPLC in a DMF layer was 94.5%, and the molar percentage of the unreacted sucrose was 1.5%.

Comparative 1 (Control Example without Organic Phosphine Compound)

407.4 g (1.19 mol) of sucrose was taken and dissolved in 3542.1 g (48.46 mol) of DMF at 70° C., and 595.9 g (0.98 mol) of 1,3-diacetoxy-1,1,3,3-tetrabutyldistannoxane was dissolved in 713.0 g (9.76 mol) of DMF at 40° C. The above two solutions were uniformly mixed under the condition where the temperature was kept at 50° C.

150.0 g of DMF was taken to feed into bottom of a vacuum distillation column (the diameter of the column is 25 mm, the distillation section is 30 cm, the stripping section is 50 cm, and a glass spring filler), a water ring pump was used to vacuumize to ensure that the pressure in the column is 5 to 50 KPa, and DMF was heated in an oil bath at the temperature of 95° C., the bottom of column was regulated for total reflux for 15 to 30 min, and the temperature in the bottom of the column was controlled to be 60 to 70° C. The above mixed solution of which the temperature was kept still was preheated by a water bath coil pipe at 85° C., and the mixed solution was fed at the speed of 9 g/min to enable the mixed solution to react in a reaction kettle, extracting from the top of the column started while feeding, and the extraction rate of distillates was regulated to 26%. After 150 g of the raw materials were fed, the reaction mixed solution was started to be extracted from the bottom of the kettle, and an automatic control system was adopted for controlling to keep the feeding and discharging materials constant. After the raw materials were fed in, 50 g of DMF was taken to flush the pipeline, fully extracting from the top of the column was conducted for 10 min, the heating was stopped, and the temperature of the tower kettle was reduced to the room temperature, then the residual materials at the bottom of the kettle was uniformly mixed with the extracted materials to obtain the reaction liquid containing the tin-sucrose adduct.

The reaction liquid containing the tin-sucrose adduct was cooled to 0° C., and 138.3 g (1.35 mol) of acetic anhydride was slowly added dropwise thereto, and the temperature was kept for 4 h after completion of the addition, and 321.0 g of water was added to terminate the acylation reaction. Then, cyclohexane (2000 mL×3) was added to extract and recover the organic tin compound 1,3-diacetoxy-1,1,3,3-tetrabutyldistannoxane, the molar yield of the sucrose-6-acetate detected by HPLC in a DMF layer was 80.9%, and the molar percentage of the unreacted sucrose was 5.6%.

Example 2 (Adopting Triphenylphosphine as an Organic Phosphine Compound)

Sucrose-6-acetate was synthesized in the same manner as in Example 1 except that 585.9 g (0.98 mol) of 1,3-diacetoxy-1,1,3,3-tetrabutyldistannoxane was replaced with 818.5 g (0.99 mol) of 1,3-diacetoxy-1,1,3,3-tetraoctyldistannoxane. The molar yield of the sucrose-6-acetate detected by HPLC in a DMF layer was 93.9%, and the molar percentage of the unreacted sucrose was 0.5%.

Example 3 (Adopting Tricyclohexylphosphine as an Organic Phosphine Compound)

203.5 g (0.59 mol) of sucrose was taken and dissolved in 1780.9 g (24.37 mol) of DMF at 70° C., and 301.2 g (0.50 mol) of 1,3-diacetoxy-1,1,3,3-tetrabutyldistannoxane was taken and dissolved in 365.0 g (4.99 mol) of DMF at 40° C. The above two solutions were uniformly mixed under the condition where the temperature was kept at 50° C., then 7.8 g (0.028 mol) of tricyclohexylphosphine was added thereto, stirred and dissolved to obtain a DMF mixed solution containing sucrose, an organic tin compound, and tricyclohexylphosphine.

150.0 g of DMF was taken to feed into bottom of a vacuum distillation column (the diameter of the column is 25 mm, the distillation section is 30 cm, the stripping section is 50 cm, and a glass spring filler), a water ring pump was used to vacuumize to ensure that the pressure in the column is 5 to 50 KPa, and DMF was heated in an oil bath at the temperature of 95° C., the bottom of column was regulated for total reflux for 15 to 30 min, and the temperature in the bottom of column was controlled to be 60 to 70° C. The above mixed solution of which the temperature was kept still was preheated by a water bath coil pipe at 85° C., and the mixed solution was fed at the speed of 8 g/min to enable the mixed solution to react in a reaction kettle, extracting from the top of the column started while feeding, and the extraction rate of distillates was regulated to 25%. After 150 g of the raw materials were fed, the reaction mixed solution was started to be extracted from the bottom of the kettle, and an automatic control system was adopted for controlling to keep the feeding and discharging materials constant. After the raw materials were fed in, 50 g of DMF was taken to flush the pipeline, fully extracting from the top of the column was conducted for 10 min, the heating was stopped, and the temperature of the bottom of column was reduced to the room temperature, then the residual materials at the bottom of the kettle was uniformly mixed with the extracted materials to obtain the reaction liquid containing the tin-sucrose adduct.

The reaction liquid containing the tin-sucrose adduct was cooled to 0° C., and 69.3 g (0.68 mol) of acetic anhydride was slowly added dropwise thereto, and the temperature was kept for 3 h after completion of the addition, and 168.9 g of water was added to terminate the acylation reaction. Then, cyclohexane (1000 mL×3) was added to extract and recover the organic tin compound 1,3-diacetoxy-1,1,3,3-tetrabutyldistannoxane, the molar yield of the sucrose-6-acetate detected by HPLC in a DMF layer was 92.4%, and the molar percentage of the unreacted sucrose was 2.0%.

Example 4 (Adopting Tricyclohexylphosphine as an Organic Phosphine Compound)

Sucrose-6-acetate was synthesized in the same manner as in Example 3 except that 301.2 g (0.50 mol) of 1,3-diacetoxy-1,1,3,3-tetrabutyldistannoxane was replaced with 415.2 g (0.50 mol) of 1,3-diacetoxy-1,1,3,3-tetraoctyldistannoxane. The molar yield of the sucrose-6-acetate detected by HPLC in a DMF layer was 93.0%, and the molar percentage of the unreacted sucrose was 1.3%.

Example 5 (Adopting Tributylphosphine as an Organic Phosphine Compound)

409.3 g (1.20 mol) of sucrose was taken and dissolved in 3554.8 g (48.64 mol) of DMF at 70° C., and 582.1 g (0.97 mol) of 1,3-diacetoxy-1,1,3,3-tetrabutyldistannoxane was taken and dissolved in 710.0 g (9.71 mol) of DMF at 40° C. The above two solutions were uniformly mixed under the condition where the temperature was kept at 50° C., then 10.3 g (0.05 mol) of tributylphosphine was added thereto, stirred and dissolved to obtain a DMF mixed solution containing sucrose, an organic tin compound, and tributylphosphine.

150.0 g of DMF was taken to feed into bottom of a vacuum distillation column (the diameter of the column is 25 mm, the distillation section is 30 cm, the stripping section is 50 cm, and a glass spring filler), a water ring pump was used to vacuumize to ensure that the pressure in the column is 5 to 50 KPa, and DMF was heated in an oil bath at the temperature of 95° C., the bottom of column was regulated for total reflux for 15 to 30 min, and the temperature in the bottom of column was controlled to be 60 to 70° C. The above mixed solution of which the temperature was kept still was preheated by a water bath coil pipe at 85° C., and the mixed solution was fed at the speed of 9 g/min to enable the mixed solution to react in a reaction kettle, extracting from the top of the column started while feeding, and the extraction rate of distillates was regulated to 28%. After 150 g of the raw materials were fed, the reaction mixed solution was started to be extracted from the bottom of the kettle, and an automatic control system was adopted for controlling to keep the feeding and discharging materials constant. After the raw materials were fed in, 50 g of DMF was taken to flush the pipeline, fully extracting from the top of the column was conducted for 10 min, the heating was stopped, and the temperature of the bottom of the column was reduced to the room temperature, then the residual materials at the bottom of the kettle was uniformly mixed with the extracted materials to obtain the reaction liquid containing the tin-sucrose adduct.

The reaction liquid containing the tin-sucrose adduct was cooled to 0° C., and 137.9 g (1.35 mol) of acetic anhydride was slowly added dropwise thereto, and the temperature was kept for 4 h after completion of the addition, and 327.7 g of water was added to terminate the acylation reaction. Then, cyclohexane (2000 mL×3) was added to extract and recover the organic tin compound 1,3-diacetoxy-1,1,3,3-tetrabutyldistannoxane, the molar yield of the sucrose-6-acetate detected by HPLC in a DMF layer was 94.8%, and the molar percentage of the unreacted sucrose was 0.6%.

Example 6 (Adopting Tributylphosphine as an Organic Phosphine Compound)

Sucrose-6-acetate was synthesized in the same manner as in Example 5 except that 582.1 g (0.97 mol) of 1,3-diacetoxy-1,1,3,3-tetrabutyldistannoxane was replaced with 816.5 g (0.99 mol) of 1,3-diacetoxy-1,1,3,3-tetraoctyldistannoxane. The molar yield of the sucrose-6-acetate detected by HPLC in a DMF layer was 95.3%, and the molar percentage of the unreacted sucrose was 0.3%.

Example 7 (Adopting Benzoic Anhydride as an Acid Anhydride Compound)

407.9 g (1.19 mol) of sucrose was taken and dissolved in 3562.3 g (48.74 mol) of DMF at 70° C., and 581.0 g (0.97 mol) of 1,3-diacetoxy-1,1,3,3-tetrabutyldistannoxane was taken and dissolved in 712.0 g (9.74 mol) of DMF at 40° C. The above two solutions were uniformly mixed under the condition where the temperature was kept at 50° C., then 10.3 g (0.05 mol) of tributylphosphine was added thereto, stirred and dissolved to obtain a DMF mixed solution containing sucrose, an organic tin compound, and tributylphosphine.

150.0 g of DMF was taken to feed into bottom of a vacuum distillation column (the diameter of the column is 25 mm, the distillation section is 30 cm, the stripping section is 50 cm, and a glass spring filler), a water ring pump was used to vacuumize to ensure that the pressure in the column is 5 to 50 KPa, and DMF was heated in an oil bath at the temperature of 95° C., the bottom of the column was regulated for total reflux for 15 to 30 min, and the temperature in the bottom of the column was controlled to be 60 to 70° C. The above mixed solution of which the temperature was kept still was preheated by a water bath coil pipe at 85° C., and the mixed solution was fed at the speed of 9 g/min to enable the mixed solution to react in a reaction kettle, extracting from the top of the column started while feeding, and the extraction rate of distillates was regulated to 28%. After 150 g of the raw materials were fed, the reaction mixed solution was started to be extracted from the bottom of the kettle, and an automatic control system was adopted for controlling to keep the feeding and discharging materials constant. After the raw materials were fed in, 50 g of DMF was taken to flush the pipeline, fully extracting from the top of the column was conducted for 10 min, the heating was stopped, and the temperature of the bottom of the column was reduced to the room temperature, then the residual materials at the bottom of the kettle was uniformly mixed with the extracted materials to obtain the reaction liquid containing the tin-sucrose adduct.

The reaction liquid containing the tin-sucrose adduct was cooled to 0° C., and 303.1 g (1.34 mol) of benzoic anhydride was slowly added dropwise thereto, and the temperature was kept for 4 h after completion of the addition, and 325.9 g of water was added to terminate the acylation reaction. Then, cyclohexane (2000 mL×3) was added to extract and recover the organic tin compound 1,3-diacetoxy-1,1,3,3-tetrabutyldistannoxane, the molar yield of the sucrose-6-benzoate detected by HPLC in a DMF layer was 92.7%, and the molar percentage of the unreacted sucrose was 1.1%.

Although detailed examples of the present disclosure have been set forth hereinabove, the description is intended to be illustrative only and is not intended to be limiting. It will be apparent to those skilled in the art that certain modifications and variations can be made without departing from the spirit of the present disclosure, and it is intended that all methods of making sucrose-6-esters having the characteristics set forth herein fall within the scope of the present application.

What is claimed is:

1. A method for synthesizing sucrose-6-ester, the method comprising:
   (a) in the presence of a polar aprotic solvent, contacting an organic phosphine compound represented by formula I with sucrose and an organic tin compound;
   (b) removing water to obtain a reaction liquid containing a tin-sucrose adduct; and
   (c) contacting the reaction liquid containing the tin-sucrose adduct with an acid anhydride compound to prepare a sucrose-6-ester;

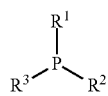

I

In formula I, $R^1$, $R^2$, and $R^3$ are each a linear or branched alkyl having 1 to 20 carbon atoms, a cycloalkyl having 3 to 10 carbon atoms or an aryl having 6 to 10 carbon atoms; and the $R^1$, $R^2$, and $R^3$ are identical groups, partially identical groups, or different groups from each other.

2. The method according to claim 1, wherein the organic phosphine compound is triphenylphosphine, tricyclohexylphosphine, or tributylphosphine.

3. The method according to claim 1, wherein a molar ratio of an amount of the organic phosphine compound I to an amount of the sucrose is 0.02 to 0.15:1.

4. The method according to claim 1, wherein the polar aprotic solvent is N,N-dimethylformamide, N,N-dimethylacetamide, or dimethyl sulfoxide; and
   a molar ratio of an amount of the polar aprotic solvent to an amount of the sucrose is 2 to 100:1.

5. The method according to claim 1, wherein the organic tin compound is 1,3-diacetoxy-1,1,3,3-tetrakis(C1-C8)alkyldistannoxane; and
   a molar ratio of an amount of the organic tin compound to an amount of the sucrose is 0.5 to 3.0:1.

6. The method according to claim 1, wherein the removing of water in the step (b) is carried out intermittently, or continuously.

7. The method according to claim 1, wherein the removing of water in the step (b) is carried out under conditions of a temperature of 45 to 90° C. and a pressure of 1 to 300 KPa.

8. The method according to claim 1, wherein in the step (b), the removing of water is carried out so that the water content in the reaction liquid containing the tin-sucrose adduct is ≤0.3 wt %.

9. The method according to claim 1, wherein in the step (c), the acid anhydride compound is acetic anhydride or benzoic anhydride; and
   a molar ratio of an amount of the acid anhydride compound to an amount of the sucrose is 0.80 to 1.50:1.

10. The method according to claim 1, wherein in the step (c), a reaction temperature is −10 to 20° C., and a reaction time is 1 to 10 h.

11. The method according to claim 1, wherein in formula I, R1, R2, and R3 are each a linear or branched alkyl having 1 to 12 carbon atoms, a cycloalkyl having 3 to 6 carbon atoms or an aryl having 6 to 7 carbon atoms.

12. The method according to claim 1, wherein a molar ratio of an amount of the organic phosphine compound I to an amount of the sucrose is 0.03 to 0.07:1.

13. The method according to claim 1, wherein the polar aprotic solvent is N,N-dimethylformamide; and
   a molar ratio of an amount of the polar aprotic solvent to an amount of the sucrose is 30 to 65:1.

14. The method according to claim 1, wherein a molar ratio of an amount of the polar aprotic solvent to an amount of the sucrose is 40 to 50:1.

15. The method according to claim 1, wherein the organic tin compound is 1,3-diacetoxy-1,1,3,3-tetrabutyldistannoxane or 1,3-diacetoxy-1,1,3,3-tetraoctyldistannoxane; and
   a molar ratio of an amount of the organic tin compound to an amount of the sucrose is 0.7 to 1.1:1.

16. The method according to claim 1, wherein the removing of water in the step (b) is carried out continuously.

17. The method according to claim 1, wherein the removing of water in the step (b) is carried out by continuous distillation.

18. The method according to claim 1, wherein the removing of water in the step (b) is carried out under conditions of a temperature of 50 to 80° C. and a pressure of 5 to 50 KPa.

19. The method according to claim 9, wherein in the step (c), a molar ratio of an amount of the acid anhydride compound to an amount of the sucrose is 1.08 to 1.17:1; and
   in the step (c), a reaction temperature is −5 to 10° C., and a reaction time is 2 to 6 h.

20. The method according to claim 1, wherein in formula I, R1, R2, and R3 are each methyl, ethyl, propyl, n-butyl, isobutyl, tert-butyl, hexyl, cyclohexyl, octyl, n-undecyl, phenyl, p-methylphenyl, or p-methoxyphenyl.

* * * * *